United States Patent [19]

Kozam et al.

[11] 4,109,653
[45] Aug. 29, 1978

[54] SUCCESSIVE DELIVERY MULTIPLE BARREL SYRINGE

[76] Inventors: George Kozam, Tenafly; Pat Romanelli, Harrington Park, both of N.J.

[21] Appl. No.: 770,741

[22] Filed: Feb. 22, 1977

[51] Int. Cl.² ............................................. A61M 5/00
[52] U.S. Cl. .......................... 128/218 R; 128/218 NV
[58] Field of Search ........... 128/218 R, 218 M, 218 P, 128/218 PA, 218 C, 218 NV, 234, 215, 220, 221; 222/135, 137, 386, 387

[56] References Cited

U.S. PATENT DOCUMENTS

| 1,496,126 | 6/1924 | Livingstone | 128/234 |
| 2,112,160 | 3/1938 | Johnson | 128/234 |
| 3,159,312 | 12/1964 | Van Sciver | 222/137 |
| 3,818,907 | 6/1974 | Walton | 128/234 X |

FOREIGN PATENT DOCUMENTS

| 1,054,173 | 2/1954 | France | 128/218 M |
| 419,869 | 10/1924 | Fed. Rep. of Germany | 128/218 M |

Primary Examiner—John D. Yasko
Attorney, Agent, or Firm—Edward F. Levy

[57] ABSTRACT

A successive delivery multiple barrel syringe includes a body which contains a pair of bores, each of which contains a plunger and each of which leads to a one-way valve and then to a single needle which is mounted on the body. Depressing the plungers in turn, pressurizes fluid placed in the bores which flows from the bores, through the one-way valves and finally through the needle. Mixing of fluids within the device is made negligible by the use of the one-way valve, and by the provision of small conduits which lead from the one-way valves to the needle.

10 Claims, 6 Drawing Figures

SUCCESSIVE DELIVERY MULTIPLE BARREL SYRINGE

Dental root canal therapy requires the removal, by lavage stream, of debrided particles of live or dead pulp tissue and dentine filings. This is most commonly brought about by varying pressures of manually propelled hydrogen peroxide, 4% solution, followed immediately by a chlorinated soda solution such as sodium hypochlorite, 5% solution. These fluids are introduced into the root canal by a small bore hypodermic needle whose tip is placed loosely in the apical one-third portion of the canal. The fluids are discharged from the hypodermic needle and carry out debris as well as sterilize the canal. The mixture of hydrogen peroxide and sodium hypochlorite liberates oxygen and chlorine which bring about the sterilization. Moreover, the weak acidic reaction helps to dissolve dead tissues. The bubbling action caused by the mixing of the solutions in the canal is of great importance in dislodging particles and the closer in time the solutions are mixed, the greater the benefit.

Normally two syringes are used in root canal therapy and the syringes are alternated several times after each operational procedure in the endodontic treatment. Ten, fifteen and sometimes even twenty installations of the syringes are made in treating the average single canal. Teeth having two, three or more canals require proportionally more installations of syringes with consequently increased expenditure of time and effort on the part of the dentist and increased trauma for the patient.

It is a principle object of the present invention to provide a successive delivery multiple barrel syringe which reduces the time and effort required for root canal therapy by a factor of approximately one-half as a result of discharging the two solutions required in succession through a single hypodermic needle. Another object of the present invention is to provide a successive delivery multiple barrel syringe which increases the power of sterilization fluids used in root canal therapy by shortening the time between interaction of fluids.

Another object of the present invention is to provide a successive delivery multiple barrel syringe which reduces the number of syringes needed in the practice of endodontics with a consequent saving in their loading, sterilization and use.

Another object of the present invention is to provide a successive delivery multiple barrel syringe in which the residual solution within the syringe bocy is negligibly small.

Another object of the present invention is to provide a successive delivery multiple barrel syringe which may be adapted for a plurality of barrels each containing a different medication for successive delivery through a single needle.

Another object of the present invention is to provide a successive delivery multiple barrel syringe which includes a plurality of bores containing various fluids and a suction channel for removal of materials through the same needle used for successive delivery of the fluids.

Another object of the present invention is to provide a successive delivery multiple barrel syringe which can be used to deliver multiple successive medications to various portions of the body including body cavities such as the middle ear, urinary tract and nasaphonynx sinuses with accuracy and precision as to quantities, and to body tissues such as the skin, muscles and the heart with only one penetration of a needle.

Another object of the present invention is to provide a successive delivery multiple barrel syringe which may be adapted to use capsules of medicine in the barrels thereof.

Another object of the present invention is to provide a successive delivery multiple barrel syringe which is completely controlled and operable by one hand of the user, employing thumb pressure.

Another object of the present invention is to provide a successive delivery multiple barrel syringe in which thumb rest portions of the pistons have different configurations to prevent accidental discharge of erroneous medications.

Another object of the present invention is to provide a successive delivery multiple barrel syringe which is comparable is size, shape and handling to the anesthetic syringes commonly used in dentistry, and which therefore does not present a frightening appearance to the patient.

Still another object of the present invention is to provide a successive delivery multiple barrel syringe which can be sterilized up to a temperature of approximately 250° F, and which is relatively sturdy and non-breakable.

A further object of the present invention is to provide a successive delivery multiple barrel syringe which may include a chamber filled with a solution such as physiologic saline for the purpose of flushing out the needle lumen.

In accordance with the present invention there is provided a successive delivery multiple barrel syringe having a body portion containing a pair of bores, with each bore containing a plunger. The bores lead to a valve body which communicates with a fitting mounting an injection needle. The valve body includes a pair of one-way valves which permit the flow of fluids from the bores to the needle and prevent flow in the reverse direction.

In use, the plungers are depressed manually in succession. As the plunger in the first bore is depressed, fluid which has been previously placed in the bore is forced out of the bore, opening the one-way valve, and flowing into the valve body and finally through the needle. The fluid in the valve body is under pressure created by the plunger and acts on the one-way valve in the second bore holding it closed and preventing the flow of fluid from the first bore to the second bore. The one-way valves thus prevent unwanted mixing of the fluids in the two bores. The amount of residual fluid which is present in the device is held to a minimum by making the proportions of the valve body cavities extremely small so that the effect of the mixing of the two fluids within the valve body is negligible.

Additional objects and advantages of the invention will become apparent during the course of the following specification when taken in connection with the accompanying drawings, in which.

Figure 1:
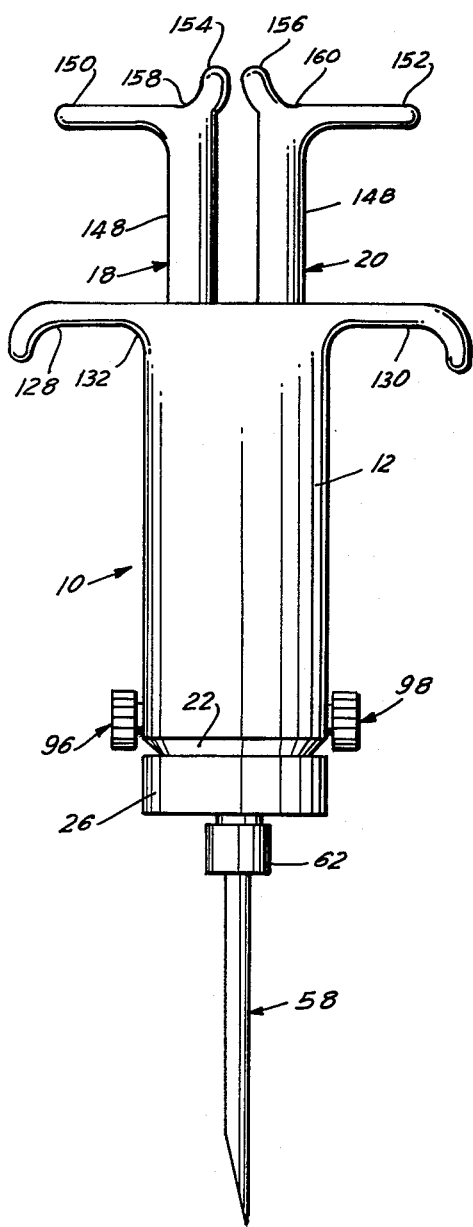
FIG. 1 is an elevational view of a successive delivery multiple barrel syringe made in accordance with the present invention.
Figure 2:
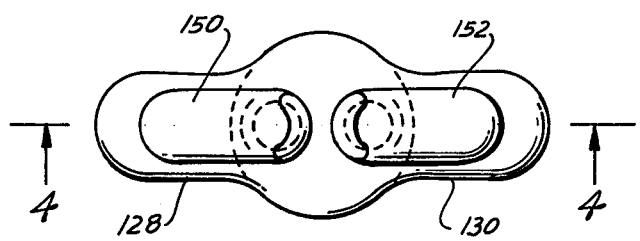
FIG. 2 is a top plan view of the successive delivery multiple barrel syringe of FIG. 1.
Figure 3:
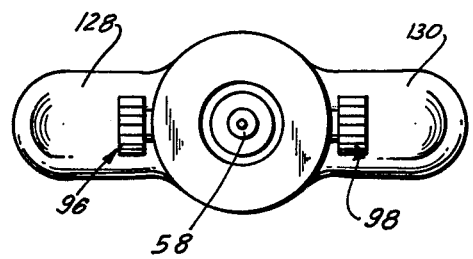
FIG. 3 is a bottom plan view of the successive delivery multiple barrel syringe of FIG. 1.

Referring in detail to the drawings there is shown in FIG. 1 a successive delivery multiple barrel syringe 10 made in accordance with the present invention and comprising a body 12 having dual bores 14,16 each of which contains a plunger 18,20.

Figure 4:
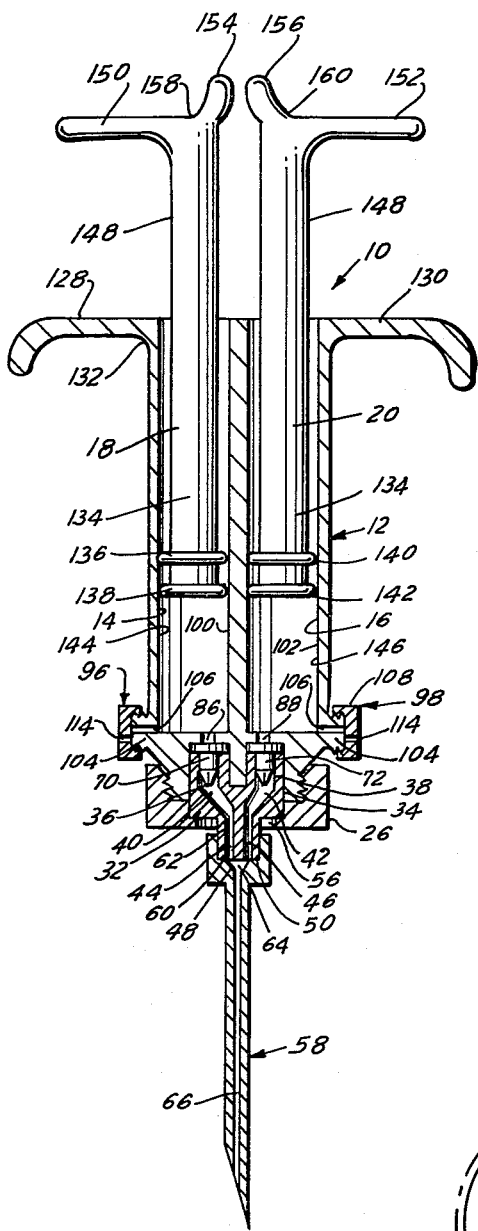
FIG. 4 is a cross-sectional view taken along the line 4—4 of FIG. 2.
Figure 5:
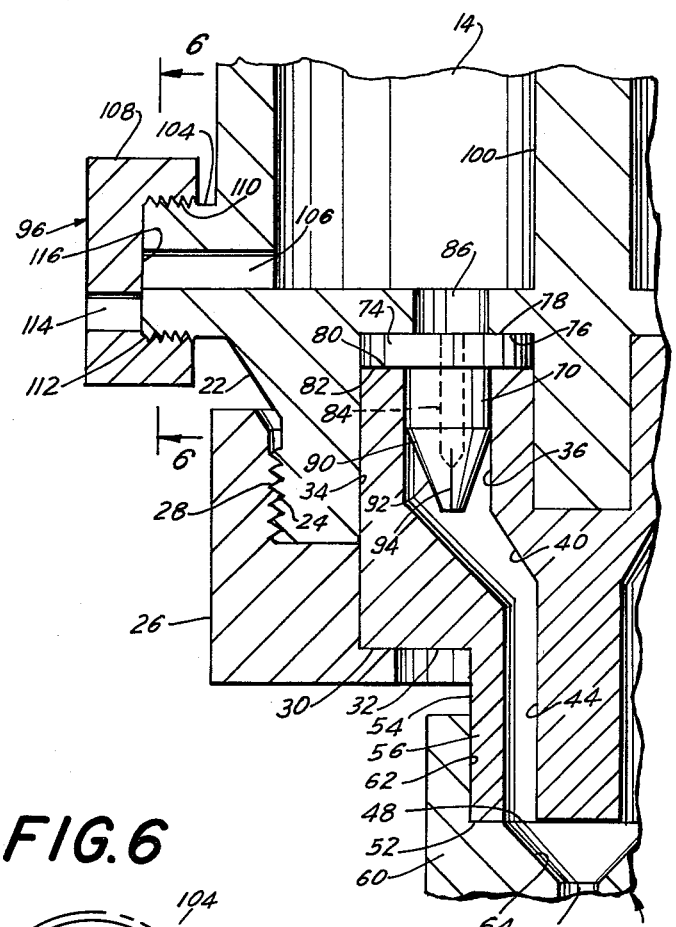
FIG. 5 is an enlarged fragmentary view of a portion of the syringe shown in FIG. 4, showing details of internal construction.

As shown in FIGS. 4 and 5, the syringe body 12 has a tapered lower end portion 22 provided with an externally-threaded portion 24 on which there is mounted a retainer 26. The retainer 26 has a threaded portion 28 and a step portion 30 which bears on a valve body 32 constituting an essential feature of the present invention. The valve body 32 extends into a cavity 34 formed in the lower portion 22 of the body 12, and is clamped in mounted position within cavity 34 by the retainer 26.

The valve body 32 includes a pair of upper valve bores 36,38 which are substantially parallel and which communicate respectively with inwardly tapering bores 40,42, which in turn communicate respectively with a pair of lower valve bores 44,46 of reduced diameter. The lower valve bores 44,46 are substantially parallel to the upper valve bores 36,38 and are closely spaced from each other.

The stepped shape of the valve body 32 forms a lower valve body extension 56 which is cylindrical and of reduced diameter, and which projects outwardly beyond the retainer 26. The valve bores 44,46 extend through the extension 56 and lead to openings 48,50 in the lower surface 52 of the valve body extension 56.

The outer surface of the lower extension 56 of the valve body 32 is adapted for mounting the body of a hypodermic type needle using one of a number of standard mouting connections, for example, a conventional Luers fitting. The lower extension 56 of the valve body 32 may be formed as a Luers fitting, thus accomodating a Luers type needle 58 having an enlarged end body poriton 60 formed with a circular cavity 62 therein. Formed centrally in the bottom wall of cavity 62 is an inwardly tapered portion 64 communicating with the axial feed bore 66 of the needle. The outer end of the tapered portion 64 has a diameter which matches or slightly exceeds the maximum distance between the opposed wall surfaces of the lower valve bores 44,46, thus permitting the two lower valve bores 44,46 to communicate with the feed bore 66 of the needle 58.

A one-way valve 70,72 is mounted in each of the upper valve bores 36,38 and is disposed to permit fluid to flow in a direction from the associated syringe bore 14,16 to the needle 58, and to prevent the flow of fluid in the reverse direction. The one-way valves 70,72, shown by way of example, in FIGS. 4 and 5 are duckbill type valves. Details of the construction and operation of the one-way valves 70,72 will be described with reference to FIG. 5 in which the one-way valve 70 is shown in enlarged scale. The one-way valve 70 includes a top flange portion 74 having an upper surface 76 which bears on the inner surface 78 of the cavity 34 in body 12, and a lower surface 80 which bears on the upper surface 82 of the valve body 32. Each of the one-way valves 70,72 is hollow and has a central bore 84 which communicates with the respective syringe bore 14,16 below which the valve is mounted, via respective orifices 86,88.

Each one-way valve 70,72 terminates in a tapered end portion 92 formed with a slit 94 which communicates with the central bore 84. In the normal, unstressed state of the valve, which is shown in FIG. 5, the slit 94 is closed and fluid in the central bore 84 can not leave the one-way valve 70. When the fluid in the bore 84 is placed under pressure by one of the plungers 18,20, the tapered lower portion 92 of the valve 70 is flexed outwardly and the fluid is forced out through the slit 94. Fluid or gas in the upper valve bore 36 attempting to flow in the reverse direction bears against the tapered end portion 92, forcing the slit 94 closed and thus preventing flow from the valve body 32 into the bore 14.

The one-way valves 70,72 may be molded in any one of a number of elastomeric materials characterized, in part, by resistance to temperatures of at least 250° F as used in sterilization, resistance to fluid solutions used in medicine and dentistry, and resistance to fluids used in sterilization.

The retainer 26 causes the valve body 32 to bear tightly against the flange 74 of the one-way valves 70,72, preventing unwanted leakage. The volume of the bores 36,38,40,42,44 and 46 is held to minimum through the application of close tolerances in the fabrication of the valve body 32, thus reducing to a negligibly small amount the volume of the residual fluid present in the device 10 during use. The mixing of fluids within the valve body 32 is considered undesirable for the application of the device 10 in the field of dentistry, and such mixing of fluids is reduced to practically zero as a result of the application of the principles of the present invention.

Figure 6:
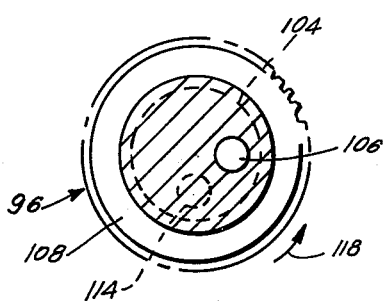
FIG. 6 is a section taken along the line 6—6 of FIG. 5.

The body 12 includes a pair of bleed valves 96,98 which facilitate venting the lower portions 100,102 of the bores 14,16 to atmosphere, thus overcoming the partial vacuum that would otherwise be created when the plungers 18,20 are withdrawn from the bores 14,16. The bleed valves 96,98 are provided on opposite sides of the syringe, and each is associated with a respective bore 14,16. Details of the construction and operation of the bleed valves 96,98 will be described with reference to FIGS. 5 and 6 in which the bleed valve 96 is shown in an enlarged scale.

Each bleed valve 96 and 98 includes a cylindrical valve body 104 formed integrally with the body 12 and projecting outwardly therefrom. Each valve body 104 has an off-center through bore 106 communicating with the lower portion 100 or 102 of the communicating bore 14 or 16. Each valve body 104 is also provided with external threading 110. A cylindrical, cupshaped cap 108 fits over the projecting valve body 104 and is rotatably attached to the valve body 104 by means of internal threading 112 on the cap 108. The cap 108 is provided with an orifice 114 which is disposed off-center thereon. When the cap 108 is screwed tightly down on the valve body 104, as shown in FIG. 5, the orifice 114 is out of registry with the bleed bore 106, and the inner wall surface 116 of the cap 108 firmly engages the opposed outer wall surface of the valve body 104, overlying the mouth of the bleed bore 106 and sealing the same against passage of air or fluids. By rotating the cap 108 slightly in the direction of the arrow 118 in FIG. 6, the cap 108 is unscrewed sufficiently to move its inner surface 116 away from the outer surface of the valve body 104, thereby bringing the offset orifice 114 into communication with the bleed bore 106 and venting the lower portion 100 of the bore 14 to atmosphere. The plunger 18 may now be freely withdrawn from the bore 14. The other bleed valve assembly 98 may be similarly manipulated to permit the plunger 20 to be freely withdrawn from the bore 16.

The syringe body 12 includes integrally formed finger grips 128,130 which project outwardly from the upper end 132 of the body 12 and which facilitate holding the syringe 10 tightly during use.

The lower portion 134 of each of the plungers 18,20 includes respective annular seals 136,138,140 and 142 which closely fit the inside surfaces 144,146 of the bores 14,16. The upper portions 148 of the plungers 18,20 extend outside of the bores 14,16 and include transversely-projecting thumb rest portions 150, 152 which are substantially perpendicular to the longitudinal axes of the plungers 18,20. The thumb rest portions 150,152 each include a projecting guard 154,156, disposed on inner ends 158,160 of the thumb rest portions 150,152, to prevent manual pressure from being applied by an operator, simultaneously to both plungers, thereby insuring that a desired single plunger is depressed at one time, and preventing the discharge of undesired solutions on medications.

In use of the syringe 10, the plungers 18 and 20 are withdrawn from the respective bores 14,16 and the latter are filled with the desired solutions. The plungers are then replaced in their respective bores, the bleed valves 96,98 being at this time in their tightly-closed positions. Medication from one of the bores, for example the bore 14, may now be administered by depressing the plunger 18, utilizing the thumb rest 150. The medicated fluid is forced through orifice 86 and one-way valve 70, into upper valve bore 36, tapered bore 40, lower valve bore 44, and thence to the tapered cavity 64 and feed bore 66 of the needle 58. The opposed one-way valve 72 prevents the fluid from being forced into the opposite syringe bore 16 during this administration. When it is then desired to administer the fluid medication in the syringe bore 16, a similar operation is performed by depressing the plunger 20 by means of its thumb rest 152. To empty or refill the bores 14 and 16, the bleed valves 96 and 98 are opened, and the plungers 18 and 20 are withdrawn. To clean or sterilize the syringe assembly, the retainer 26 is unscrewed and removed, and the valve body 32 is removed from the syringe body 12.

In an alternative embodiment, which is not shown, the thumb rests incorporate surfaces which permit tactile discrimination between the two thumb rests. An example of such surfaces includes surfaces formed with undulations of different pitch. Another example comprises a knurled portion formed on one of the thumb rests and a smooth surface formed on a corresponding surface of the other thumb rest.

In another alternative embodiment of the invention, semi-automatic operation of the successive delivery multiple barrel syringe is provided by removing the plungers 18,20 and substituting a push button type valve and connections leading to tubing which connects the bores to remote pressurized containers or reservoirs which store the solutions to be injected. The push button type valves are normally closed and may be opened by manual pressure to permit fluids to flow from the pressurized containers into the bores and ultimately through the needle. Alternatively, non-pressurized containers may be used with the non-pressurized containers being selectively pressurized to cause fluids to flow into the bores.

In still another embodiment of the present invention, the device instead of being adapted for a pair of bores, as is shown in the drawings, may be adapted for a plurality of bores each containing a different solution, or capsule of medicine, for successive delivery through a single needle. In addition, the body of the device may include a suction channel. The suction channel includes a valve which prevents fluid flow into the suction channel during the injection of fluids and which may be opened permitting the suction channel to communicate with the needle which is used for injection. The suction channel may be used to retrieve solutions in the tooth canal and in periapical abscesses.

While preferred embodiments of the invention have been shown and described herein, it is obvious that numerous additions, changes and omissions may be in such embodiments without departing from the spirit and scope of the invention.

What is claimed is:

1. A successive delivery multiple barrel syringe comprising a body having a plurality of parallel bores, a plurality of individually-depressible plungers extending respectively into said bores, said body having an externally-threaded lower end portion formed with a bottom cavity, a valve body member extending into said cavity and having a plurality of through bores, each communicating with one of the parallel bores of said syringe body, a retainer member having an internally-threaded portion engaging the externally-threaded lower end portion of said syringe body and underlying a portion of said valve body member for releasably clamping the latter in a mounted position within said cavity, said valve body member having a lower body extension projecting below said retainer member and including needle mounting means, a hollow needle mounted on said needle mounting means, the through bores of said valve body member connecting each of the respective bores of said syringe body with said hollow needle, and a plurality of one-way valve means, disposed, one each, in said through bores of said valve body member, and disposed to permit the flow of fluid from each of said parallel bores of said syringe body to said needle and to prevent the flow of fluid in the reverse direction, thereby permitting selective successive depression of said plungers to cause fluids placed in said parallel bores to flow in succession through said needle without mixing of said fluids within said syringe body.

2. A successive delivery multiple barrel syringe comprising a body having a plurality of bores, a plurality of plungers extending respectively into said bores, needle mounting means disposed on said body, a hollow needle mounted on said needle mounting means, conduit means connecting each of the respective bores with said hollow needle, a plurality of one-way valve means, disposed, one each, in said conduit means, and disposed to permit the flow of fluid from each of said bores to said needle and to prevent the flow of fluid in the reverse direction, thereby permitting selective successive depression of said plungers to cause fluids placed in said bores to flow in succession through said needle, and bleed valve means disposed on said body for selectively venting said bores to atmosphere, thereby facilitating the withdrawal of said plungers from said bores for the purpose of refilling said bores.

3. A successive delivery multiple barrel syringe according to claim 1 in which said one-way valve means comprises a plurality of check valves.

4. A successive delivery multiple barrel syringe according to claim 1 in which said one-way valve means comprises a plurality of elastomeric duckbill valves each having a top flange portion clamped between the inner wall of said cavity and the upper surface of said valve body member by said retainer member.

5. A successive delivery multiple barrel syringe according to claim 1 in which each of said plungers includes thumb rest means for operation of said plunger by manual pressure.

6. A successive delivery multiple barrel syringe according to claim 5 in which said thumb rest means includes an elongated thumb rest member projecting laterally from the upper end of each plunger and extending in a direction away from the opposed plunger, and a guard projection on the inner end of each thumb rest member and positioned to isolate said thumb rest members from each other and prevent inadvertent depression of both thumb rest members simultaneously.

7. A successive delivery multiple barrel syringe according to claim 1 in which said syringe body has a pair of bores arranged parallel to each other and in which the cavity of said lower end portion communicates with each of said pair of bores through respective orifices, each of said one-way valve means underlying one of said respective orifices.

8. A successive delivery multiple barrel syringe according to claim 7 in which said valve body has a pair of spaced upper valve bores, communicating with the respective syringe body bores through said orifices, and each containing said one-way valve means, and an intermediate valve bore communicating with each intermediate valve bore and with said hollow needle.

9. A successive delivery multiple barrel syringe according to claim 8 in which said hollow needle has a relatively wide, tapered inlet opening communicating with each of said lower valve bores.

10. A successive delivery multiple barrel syringe according to claim 2 in which said bleed valve means comprises an externally-threaded valve body projecting from said syringe body in registry with each of said syringe body bores, a bleed bore in each valve body communicating with the lower end of the associated syringe body bore, and internally threaded cap mounted on each valve body, and an offset aperture in said cap.

* * * * *